(12) United States Patent
Morel et al.

(10) Patent No.: US 10,088,664 B2
(45) Date of Patent: Oct. 2, 2018

(54) METHOD FOR OBSERVING A SAMPLE BY LENS-FREE IMAGING

(71) Applicant: Commissariat a l'Energie Atomique et aux Energies Alternatives, Paris (FR)

(72) Inventors: Sophie Morel, Douai (FR); Cedric Allier, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/413,914

(22) Filed: Jan. 24, 2017

(65) Prior Publication Data
US 2017/0212343 A1    Jul. 27, 2017

(30) Foreign Application Priority Data

Jan. 25, 2016  (FR) ...................... 16 50575

(51) Int. Cl.
*G02B 21/36* (2006.01)
*G01N 21/25* (2006.01)
(Continued)

(52) U.S. Cl.
CPC ......... *G02B 21/367* (2013.01); *G01N 21/255* (2013.01); *G01N 21/455* (2013.01); (Continued)

(58) Field of Classification Search
CPC .... G02B 21/367; G02B 21/33; G03H 1/0443; G03H 1/0866; G03H 1/0005;
(Continued)

(56) References Cited

U.S. PATENT DOCUMENTS

2011/0136165 A1   6/2011   Vojnovic et al.
2012/0142086 A1   6/2012   Haguet et al.
(Continued)

FOREIGN PATENT DOCUMENTS

WO   WO 2008/090330 A1   7/2008
WO   WO 2012/094523 A2   7/2012

OTHER PUBLICATIONS

French Preliminary Search Report dated Nov. 29, 2016 in French Application 16 50575, filed on Jan. 25, 2016 (with English Translation of Categories of Cited Documents and Written opinion).
(Continued)

*Primary Examiner* — Hwa Lee
(74) *Attorney, Agent, or Firm* — Oblon, McClelland, Maier & Neustadt, L.L.P.

(57) ABSTRACT

The invention relates to a method for observing a sample, in particular an anatomopathological slide formed from a thin thickness of a sampled biological tissue. It includes a step of illuminating the sample with a light source and acquiring, with an image sensor, an image representing the light transmitted by the sample. The image undergoes holographic reconstruction, so as to obtain a representation, in the plane of the sample, of the light wave transmitted by the latter. The method includes applying an impregnating fluid to the sample, such that the sample is impregnated with said impregnating liquid, said impregnating liquid having a refractive index strictly higher than 1.

12 Claims, 7 Drawing Sheets

(51) Int. Cl.
*G01N 33/483* (2006.01)
*G02B 21/33* (2006.01)
*G03H 1/00* (2006.01)
*G03H 1/04* (2006.01)
*G01N 21/45* (2006.01)
*G03H 1/08* (2006.01)
G01B 9/021 (2006.01)
G01N 15/10 (2006.01)
G01N 15/14 (2006.01)

(52) U.S. Cl.
CPC ......... *G01N 33/4833* (2013.01); *G02B 21/33* (2013.01); *G03H 1/0005* (2013.01); *G03H 1/0443* (2013.01); *G03H 1/0465* (2013.01); *G03H 1/0866* (2013.01); *G01B 9/021* (2013.01); *G01N 15/1463* (2013.01); *G01N 2015/1006* (2013.01); *G01N 2201/0627* (2013.01); *G03H 2001/005* (2013.01); *G03H 2001/0447* (2013.01); *G03H 2001/0454* (2013.01); *G03H 2001/0471* (2013.01)

(58) Field of Classification Search
CPC ......... G03H 1/0465; G03H 2001/0454; G03H 2001/0447; G03H 2001/005; G03H 2001/0471; G01N 33/4833; G01N 21/455; G01N 21/255; G01N 2201/0627; G01N 15/1463; G01N 2015/1006; G01B 9/021

See application file for complete search history.

(56) References Cited

U.S. PATENT DOCUMENTS

2012/0218379 A1  8/2012  Ozcan et al.
2013/0280752 A1  10/2013  Ozcan et al.
2014/0248713 A1  9/2014  Allier et al.
2016/0153959 A1  6/2016  Vojnovic et al.

OTHER PUBLICATIONS

Dan Zhu et al. "Recent progress in tissue optical clearing" Laser & Photonics Reviews, vol. 7, No. 5, 2013, 26 pages.

C.P. Allier et al. "Lensfree microscopy: a new framework for the imaging of viruses, bacteria, cells and tissue", 2015 IEEE International Electron Devices Meeting, 2015, 5 pages.

Olga S. Zhernovaya et al. " Study of optical clearing of blood by immersion method", Dynamics and Fluctuations in Biomedical Photonics VIII, 2011, 8 pages.

Wei Luo et al. "Synthetic aperture-based on-chip microscopy", Light: Science & Applications, 2015, 9 pages.

Alon Greenbaum et al. "Wide-field computational imaging of pathology slides using lens-free on-chip microscopy", Science translation Medicine, vol. 6, Issue 267, 2014, 11 pages.

METHOD FOR OBSERVING A SAMPLE BY LENS-FREE IMAGING

FIELD OF THE INVENTION

The technical field of the invention is related to the observation of a sample, in particular a biological sample, by lens-free imaging. The sample may especially be a biological tissue, the observation being carried out for the purposes of histological analysis.

BACKGROUND

The observation of samples, and in particular biological samples, by lens-free imaging has seen substantial development over the last ten years. This technique allows a sample placed between a light source and an image sensor to be observed without a magnifying optical lens placed between the sample and the image sensor. Thus, the image sensor collects an image of the light wave transmitted by the sample.

This image is made up of interference patterns formed by interference between the light wave emitted by the light source and transmitted by the sample, and diffracted waves resulting from the diffraction by the sample of the light wave emitted by the light source. These interference patterns are sometimes denoted diffraction patterns.

Document WO2008090330 describes a device allowing biological samples, in this case cells, to be observed by lens-free imaging. The device allows an interference pattern to be associated with each cell and the morphology of this pattern allows the type of cell to be identified. Lens-free imaging would thus appear to be a simple and inexpensive alternative to conventional microscopy. In addition, its field of observation is clearly larger than that obtainable with a microscope. Thus, it will be understood that the potential applications of this technology are broad and far-reaching.

Generally, the image formed on the image sensor, i.e. the interference pattern image, may be processed by way of a holographic reconstruction algorithm, so as to estimate optical properties of the sample. Such algorithms are well known in the field of holographic reconstruction. To do this, the distance between the sample and the image sensor being known, a propagation algorithm, taking into account this distance and the wavelength of the light wave emitted by the light source, is applied. It is then possible to create an image of an optical property of the sample. A numerical reconstruction algorithm is for example described in US 2012/0218379.

The relevance of lens-free imaging to histological analysis of cancerous tissue samples taking the form of a thin strip, or slice, deposited on a transparent holder has recently been demonstrated. The large field of observation achieved with lens-free imaging, coupled to its low cost, are decisive advantages with respect to the use of a conventional microscope. In addition, the use of holographic reconstruction algorithms makes it possible to form an absorption image or a phase image of the observed sample of a high enough quality for a reliable histological analysis to be carried out.

The publication Greenbaum A, "wide-field computational imaging of pathology slides using lens-free on-chip microscopy", Sci. Transl. Med 6, 267ra175 (2014), for example describes the application of lens-free imaging to anatomopathological slides formed by sampling various types of biological tissues. The same is also true of the publication Luo W. "Synthetic aperture-based on-chip microscopy", Light: Science & Applications (2015) 4, e261. In this publication, an optical coupling oil is applied between the image sensor and the sample so as to improve the optical coupling. However, the time required to obtain an image of a sample of 1 mm$^2$ exceeds 45 minutes, this being far too long and incompatible with routine use.

The inventors provide a method for observing a sample, and in particular a tissue sample, by lens-free imaging, implementing holographic reconstruction methods and allowing a clearer image to be formed. This method is particularly suitable for the observation of biological tissues.

SUMMARY

A first object of the invention is a method for observing a sample, and preferably a porous sample, including the following steps:
i) illuminating said sample using a light source able to emit an incident light wave that propagates towards the sample;
ii) acquiring, using an image sensor extending in a detection plane, at least one image of the sample, the sample being placed between the light source and the image sensor, each image being representative of an exposing light wave, to which the image sensor is exposed;
iii) applying a propagation operator to the image acquired in step ii) so as to form an image representative of the exposing light wave, in a plane passing through said sample;
wherein the method also comprises, prior to step ii), applying an impregnating fluid to the sample, such that the sample is impregnated with the impregnating liquid, the impregnating liquid having a refractive index strictly higher than 1, such that the sample is made transparent or translucent after the impregnating liquid has been applied, wherein the image formed in step iii), i.e. the image representative of the light wave to which the image sensor is exposed, is established from the phase, in the plane passing through the sample, of the exposing light wave.

The light wave transmitted by the sample corresponds to a light wave to which the image sensor is exposed.

The sample may be impregnated before step i) or between steps i) and ii).

Preferably, the image formed in step iii), i.e. the image representative of the light wave transmitted by the sample, i.e. the light wave to which the image sensor is exposed, is established from the phase, in the sample plane, of said light wave transmitted by the sample. Thus, step iii) allows the phase of this light wave in a plane passing through the sample to be determined. The plane passing through the sample may be a plane in which the sample extends. It is preferably substantially parallel to the detection plane.

The method may comprise applying a high-pass filter to the image formed in step iii).

According to one preferred embodiment, the sample is a slice of biological tissue.

According to one preferred embodiment, the impregnating liquid has a refractive index comprised between 1.2 and 1.8 or between 1.3 and 1.7.

According to one embodiment, said impregnating liquid extends from the sample to the image sensor. The image sensor comprises a plurality of pixels, and the impregnating liquid extends from the sample to these pixels. Each pixel may be coupled to a focusing microlens, in which case the impregnating liquid may extend from the sample to each microlens.

According to one embodiment, the impregnating liquid is applied to the sample or to the image sensor and then the distance between the sample and the image sensor is decreased until the impregnating liquid extends from the sample to the image sensor.

A transparent slide can be placed between the sample and the image sensor, the impregnating liquid extending between the sample and said transparent slide.

According to one embodiment, step ii) includes forming a plurality of images, each image being acquired in a different spectral band, step iii) then including the following substeps:

a) determining, from each image acquired in a spectral band, an initial complex amplitude of the exposing light wave in said spectral band, in the detection plane;

b) on the basis of each complex amplitude established in said detection plane, in each spectral band, determining a complex amplitude of the exposing light wave in each spectral band, in the plane in which the sample extends;

c) combining a plurality of complex amplitudes determined in substep b), in various spectral bands, in order to calculate a weighting function in the sample plane;

d) projecting said weighting function into the detection plane so as to obtain, for each spectral band, a weighting function in said detection plane;

e) updating each complex amplitude of the exposing light wave in each spectral band, in the detection plane, using said weighting function obtained, in said spectral band, in substep d);

f) repeating substeps b) to e) until an end criterion is met.

The method may include a substep g) of forming an image representative of the argument, in the plane of the sample, of the complex amplitude of the exposing light wave transmitted by the sample in at least one spectral band.

According to a preferred embodiment, no image-forming or magnifying optics are placed between the sample and the image sensor.

DETAILED DESCRIPTION OF THE ILLUSTRATED EMBODIMENTS

Figure 1A:
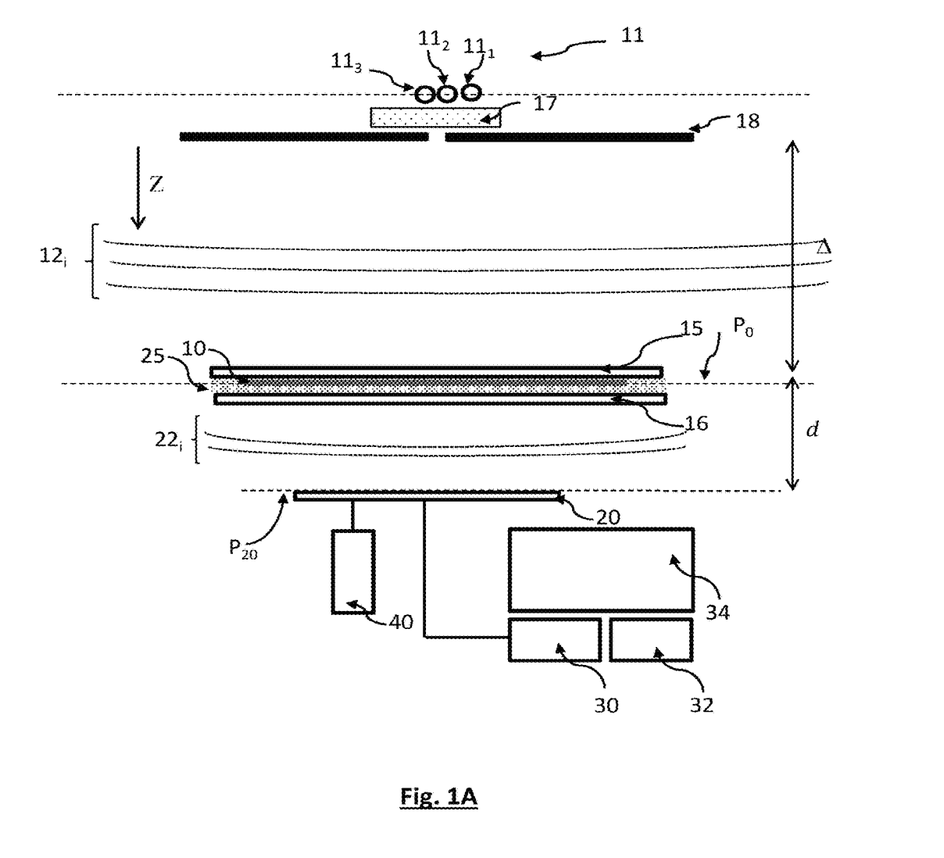
FIG. 1A shows a first exemplary device for implementing the invention, the analysed sample being an anatomopathological slide.

FIG. 1A shows an exemplary device. A light source 11 is able to emit a light wave 12, which light wave is called the incident light wave. The incident light wave propagates towards the sample 10, along a propagation axis Z.

The sample 10 may be a biological sample that it is desired to characterize. It may especially be a tissue slide intended for a histological analysis, for example an anatomopathological slide, including a thin thickness of tissue deposited on a transparent slide 15. The expression "thin thickness" is understood to mean a thickness that is preferably smaller than 100 µm, preferably smaller than 10 µm and typically a few microns. Such a sample is shown in FIG. 1A. The sample extends in a plane $P_0$, called the sample plane, perpendicular to the propagation axis Z.

This tissue slide 10 is obtained using known preparation methods from a tissue sample sampled by biopsy or swabbing, then prepared so as to take the form of a thin thickness deposited on a transparent slide, the latter serving as a holder. Such methods are known in the field of histology. They for example include sectioning a frozen tissue, or embedding a sampled tissue in a paraffin matrix.

The distance Δ between the light source 11 and the sample 10 is preferably larger than 1 cm. It is preferably comprised between 2 and 30 cm. Preferably, the light source, as seen by the sample, is considered to be point-like. This means that its diameter (or its diagonal) is preferably smaller than one tenth and better still one hundredth of the distance between the sample and the light source. Thus, preferably, the light reaches the sample in the form of plane waves, or waves which may be considered as such.

In the example in FIG. 1A, the light source 11 includes free light-emitting diodes (LEDs,) $11_1$, $11_2$ and $11_3$ that emit in a first spectral band $\lambda_1$=450 nm-465 nm, a second spectral band $\lambda_2$=520 nm-535 nm and a third spectral band $\lambda_3$=620 nm-630 nm, respectively. These three light-emitting diodes constitute elementary sources of the light source 11. In this example, the light source is a light-emitting diode (LED) sold by Cree under the reference XLamp MCE. Its three constituent elementary light-emitting diodes $11_1$, $11_2$ and $11_3$ are activated simultaneously. Alternatively, these light-emitting diodes may be activated successively.

The light source 11 is preferably point-like. It may especially comprise a diaphragm 18, or spatial filter. The aperture of the diaphragm is typically comprised between 5 µm and 1 mm and preferably between 50 µm and 500 µm. In this example, the diaphragm is that sold by Thorlabs under the reference P150S and its diameter is 150 µm. The diaphragm may be replaced by an optical fibre a first end of which is placed facing the light source 11 and a second end of which is placed facing the sample 10.

The device preferably includes a scatterer 17, which is placed between the light source 11 and the diaphragm 18. The use of such a scatterer allows constraints on the centring of the light source 11 with respect to the aperture of the diaphragm 18 to be relaxed. The function of such a scatterer is to distribute the light beam produced by an elementary light source $11_i$ ($1 \leq i \leq 3$) over a cone of angle α, α being equal to 40° in the present case. Preferably, the scattering angle α varies between 10° and 80°. In this example, the scatterer is that sold by Luminit under the reference Luminit LSD 40°.

The sample 10 is placed between the light source 11 and an image sensor 20. The latter preferably extends parallelly, or substantially parallelly to the transparent slide 15 holding the sample. The expression "substantially parallelly" means that the two elements may not be rigorously parallel, an angular tolerance of a few degrees, smaller than 20° or 10°, being allowed.

The image sensor 20 is able to form an image in a detection plane $P_{20}$. In the example shown, it is a CCD or CMOS image sensor including a matrix array of pixels. CMOS sensors are the preferred type of sensor because their pixels are of smaller size, thereby allowing images to be acquired the spatial resolution of which is more favourable. In this example, the image sensor is a CMOS sensor sold by Omnivision under the reference OV5647. It is an RGB CMOS sensor comprising 2592×1944 square pixels of 1.4 μm size. The useful area of the sensor is 3.6×2.7 mm². Sensors the size of the pixels of which is smaller than 3 μm are preferred, in order to improve the spatial resolution of the image. The detection plane $P_{20}$ preferably extends perpendicularly to the propagation axis Z of the incident light wave 12.

The image sensor includes a Bayer filter such that each pixel is sensitive to a spectral band chosen from the blue, the red or the green. Thus, when the sample is exposed to the light source 11, the image sensor 20 acquires an image I that is decomposable into:
- a first image $I_1$ in the first emission spectral band $\lambda_1$ of the first light-emitting diode $11_1$, this image being formed from the pixels exposed to a wavelength transmitted by the blue filter of the Bayer filter;
- a second image $I_2$ in the second emission spectral band $\lambda_2$ of the second light-emitting diode $11_2$, this image being formed from the pixels exposed to a wavelength transmitted by the green filter of the Bayer filter; and
- a third image $I_3$ in the third emission spectral band $\lambda_3$ of the third light-emitting diode $11_3$, this image being formed from the pixels exposed to a wavelength transmitted by the red filter of the Bayer filter.

Generally, according to this embodiment, the image sensor 20 allows images $I_i$ of the sample 10 to be acquired in various spectral bands $\lambda_i$. Each image $I_i$ is representative of a light wave, called the exposing light wave $22_i$, which is transmitted by the sample 10 and to which the image sensor is exposed, in each spectral band $\lambda_i$. Preferably, there is no overlap between the various spectral bands; a negligible overlap for example concerning less than 25% and better still less than 10% of the emitted light intensity is however envisageable.

Other configurations are possible, for example a monochromatic image sensor may be used that acquires, in the various spectral bands $\lambda_i$, an image $I_i$ of the sample as the latter is successively illuminated by an incident wave $12_i$. Each incident wave $12_i$ may be emitted by one light source $11_i$ emitting in one of said spectral bands, or by a white light source filtered by an optical filter the passband of which corresponds to said spectral band $\lambda_i$.

The distance d between the sample 10 and the matrix array of pixels of the image sensor 20 is, in this example, equal to 300 μm. Generally, and this whatever the embodiment, the distance d between the sample and the pixels of the image sensor is preferably comprised between 50 μm and 2 cm and preferably comprised between 100 μm and 2 mm.

The absence of magnifying optics between the image sensor 20 and the sample 10 will be noted. This does not rule out the optional presence of focusing microlenses level with each pixel of the image sensor 20, said lenses not having for function the magnification of the image acquired by the image sensor.

Under the effect of the incident light wave $12_i$, the sample 10 may engender a diffracted wave liable to generate, level with the detection plane $P_{20}$, interference, in particular with a portion of the incident light wave $12_i$ transmitted by the sample. Moreover, the sample may absorb some of the incident light wave $12_i$. Thus, the exposing light wave $22_i$ to which the image sensor is exposed 20, may comprise, in a spectral band $\lambda_i$:
- a component resulting from the diffraction of the incident light wave $12_i$ by the sample; and
- a component resulting from the absorption of the incident light wave $12_i$ in the sample.

A processor 30, for example a microprocessor, is configured to process each image acquired by the image sensor 20. In particular, the processor is a microprocessor connected to ar memory 32 in which a sequence of instructions allowing the image-processing and calculating operations described in this description to be carried out is stored. The processor may be coupled to a screen 34 allowing images acquired by the image sensor 20 or calculated by the processor 30 to be displayed.

The device also includes an actuator 40 allowing the sample 10 to be moved relative to the image sensor 20, this movement preferably being in a direction perpendicular to the propagation axis Z, i.e. parallel to the detection plane $P_{20}$. Such a movement makes it possible to scan a sample of large area, typically of a few cm². The field of observation of the image sensor is similar to the size of the CMOS sensor, i.e. 3.6×2.7 millimeters i.e. 9.7 mm², because of the small distance d between the sample and the sensor. It is therefore necessary to move the image sensor 20 relatively to the sample 10 if all of the latter is to be observed.

One important aspect of the invention relates to the configuration of the sample 10. Prior to the acquisition of images by the image sensor, an impregnating liquid 25 is deposited on this sample. This impregnating liquid 25 is a liquid or a gel the refractive index of which is strictly higher than 1 and preferably higher than 1.2. Advantageously, this refractive index is close to the refractive index of the sample, or comprised between the refractive index of the sample and the refractive index of the image sensor and in particular of the focusing microlenses associated with each pixel. The expression "refractive index close to that of the sample" is understood to mean comprised between +50% and −50% or +30% and −30% of the refractive index of the sample. The refractive index of the impregnating liquid 25 is for example comprised between 1 and 2. Advantageously, it is comprised between 1.2 and 1.8. When the sample 10 includes a frozen tissue, the refractive index is preferably comprised between 1.3 and 1.5. When the sample 10 is a tissue embedded in a paraffin matrix, the refractive index is preferably in the vicinity of 1.5 and for example comprised between 1.4 and 1.7.

The impregnating liquid 25 is placed in contact with the sample 10 and the latter, because of its porosity, is impregnated therewith. The sample then becomes transparent or translucent under the effect of this impregnation. The inventors have observed that such a configuration allows a good-quality image of the sample to be obtained, as described below with reference to the experimental trials that have been carried out. The impregnating liquid 25 may be chosen from a clearing agent known to clear tissues. It may for example be BABB, acronym of benzyl alcohol/benzyl benzoate, a clearing agent known to those skilled in the art. It may also be glycerol, or ethanol or DMSO, acronym of dimethyl sulfoxide. Other clearing agents known to clear tissues i.e. clearing agents, are mentioned in the publication Zhu D "Recent Progress in Tissue Optical Clearing" Laser & Photonics Reviews. 2013 7(5): 732-757.

As illustrated in FIG. 1A, the impregnating liquid 25 may fill a space comprising the sample 10, this space being bounded by the slide 15 described above called the holding slide, and another slide called the confining slide 16 which preferably extends parallelly, or substantially parallelly, to the holding slide 15 and to the detection plane $P_{20}$. This configuration allows planar interfaces to be formed between the various media through which the light wave transmitted by the sample passes before reaching the image sensor 20.

Figure 1B:
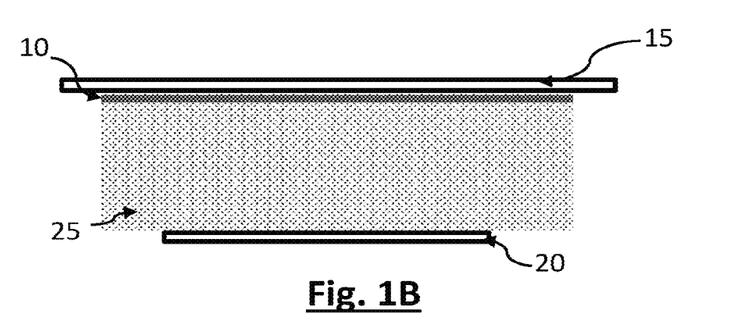
FIGS. 1B and 1C show various sample configurations.

The confining slide 16 is optional and may be omitted, as shown in FIG. 1B. In this configuration, the impregnating liquid 25 extends between the sample 10 and the image sensor 20. In this exemplary embodiment, the impregnating liquid extends as far as focusing microlenses placed facing each pixel. This makes it possible to ensure matching of the refractive index from the sample to each pixel.

Figure 1C:
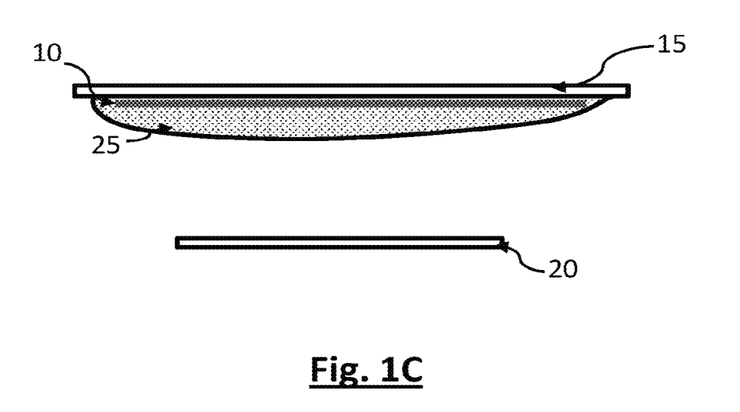

In the embodiment shown in FIG. 1C, the impregnating liquid 25 is placed in contact with the sample 10 and does not extend as far as the image sensor. However, with respect to the configurations illustrated in FIGS. 1A and 1B, this configuration has the drawback of a non-planar and poorly controlled air/impregnating liquid interface.

Use of an impregnating liquid between a sample and an image sensor is known in the prior art, and in particular from the aforementioned publication by W. Luo. However, an important element of the invention is that the sample 10 is placed in contact with the impregnating liquid 25 and impregnated with the latter, this running contrary to the prior art in which the impregnating liquid extended as far as a transparent slide bounding the sample and did not make direct contact with the sample. The impregnation of the impregnating liquid 25 into the sample 10 modifies its visual appearance by increasing its transparency, thereby decreasing the scattering of the incident light wave $12_i$ in the sample. The invention takes advantage of the fact that the impregnating liquid 25 penetrates into the sample 10, the latter being porous.

The images acquired with the image sensor 20 do not allow a sufficiently precise representation of the observed sample to be obtained, in particular when the latter is a tissue slide. As described with reference to the prior art, it is possible to apply, to each image I acquired by the image sensor in a spectral band λ, a propagation operator h, so as to calculate a quantity representative of the exposing light wave 22, i-e the light wave transmitted by the sample 10 and to which light wave the image sensor 20 is exposed. Such a method, designated by the expression holographic reconstruction, in particular allows an image of the modulus or phase of the exposing light wave to be reconstructed in a plane parallel to the detection plane $P_{20}$, and in particular in the plane $P_0$ in which the sample extends. To do this, the product of a convolution between an image I acquired by the image sensor 20, which image is designated by the term "hologram", and a propagation operator h, is calculated. It is then possible to reconstruct a complex amplitude α of the exposing light wave 22 at any point of spatial coordinates (x,y,z) and in particular in a plane located at a distance |z| from the image sensor 20, this plane possibly being the sample plane $P_0$. The complex amplitude α is a complex quantity the argument and modulus of which are respectively representative of the phase and intensity of the exposing light wave 22 to which the image sensor is exposed.

The function of the propagation operator h(x,y,z) is to describe the propagation of the light between the image sensor 20 and a point of coordinates (x,y,z) located at a distance |z| from the image sensor 20. It is then possible to determine the modulus M(x,y,z) and/or the phase φ(x,y,z) of the light wave 22 at this distance |z|, which is called the reconstruction distance, where:

$M(x,y,z) = \text{abs}[α(x,y,z)]$; and $φ(x,y,z) = \arg[α(x,y,z)]$.

The operators abs and arg designate the modulus and the argument, respectively.

The complex expression of the exposing light wave 22 at a coordinate (x,y,z) is given by $α(x,y,z) = \sqrt{I(x,y)} * h(x,y,z)$ the symbol * designating a convolution product. $\sqrt{I(x,y)}$ designates the square root of the intensity of the pixels of coordinates (x,y) of the image I acquired in the detection plane $P_{20}$, and z here designates a reconstruction distance with respect to the image sensor.

The propagation operator may for example be the Fresnel-Helmholtz function such as:

$$h(x, y, z) = \frac{1}{j\lambda z} e^{j2\pi \frac{z}{\lambda}} \exp\left(j\pi \frac{x^2 + y^2}{\lambda z}\right),$$

where λ designates wavelength.

When the reconstruction distance z corresponds to the distance d between the image sensor 20 and the sample plane $P_0$, it is possible to obtain an image $I^0$ of the modulus $M^0$ and/or phase $φ^0$ of the exposing light wave 22 transmitted by the sample in the sample plane $P_0$, each of these images, so-called reconstructed images, being a representation of this sample 10. The rest of the description, which relates to experimental trials, shows that the image representing the phase of the exposing light wave 22 in the sample plane $P_0$ is rich in information on the sample and may be used for the purposes of histological analysis.

The inventors have developed an optimized holographic reconstruction method that capitalizes on the acquisition of images $I_i$ of the sample in a plurality of spectral bands $λ_i$. For this reason, the sample is illuminated simultaneously by activating the three elementary light sources $11_1$, $11_2$ and $11_3$ described above. The image sensor 20 acquires an image I, from which three images $I_1$, $I_2$, $I_3$ are respectively formed in the first, second and third spectral bands $λ_1$, $λ_2$, $λ_3$ respectively associated with said elementary light sources, as described above. The method implemented is an iterative method, including the steps described below with reference to FIGS. 2A and 2B. It has been further described in the international patent application WO2016189257.

Figure 2A:
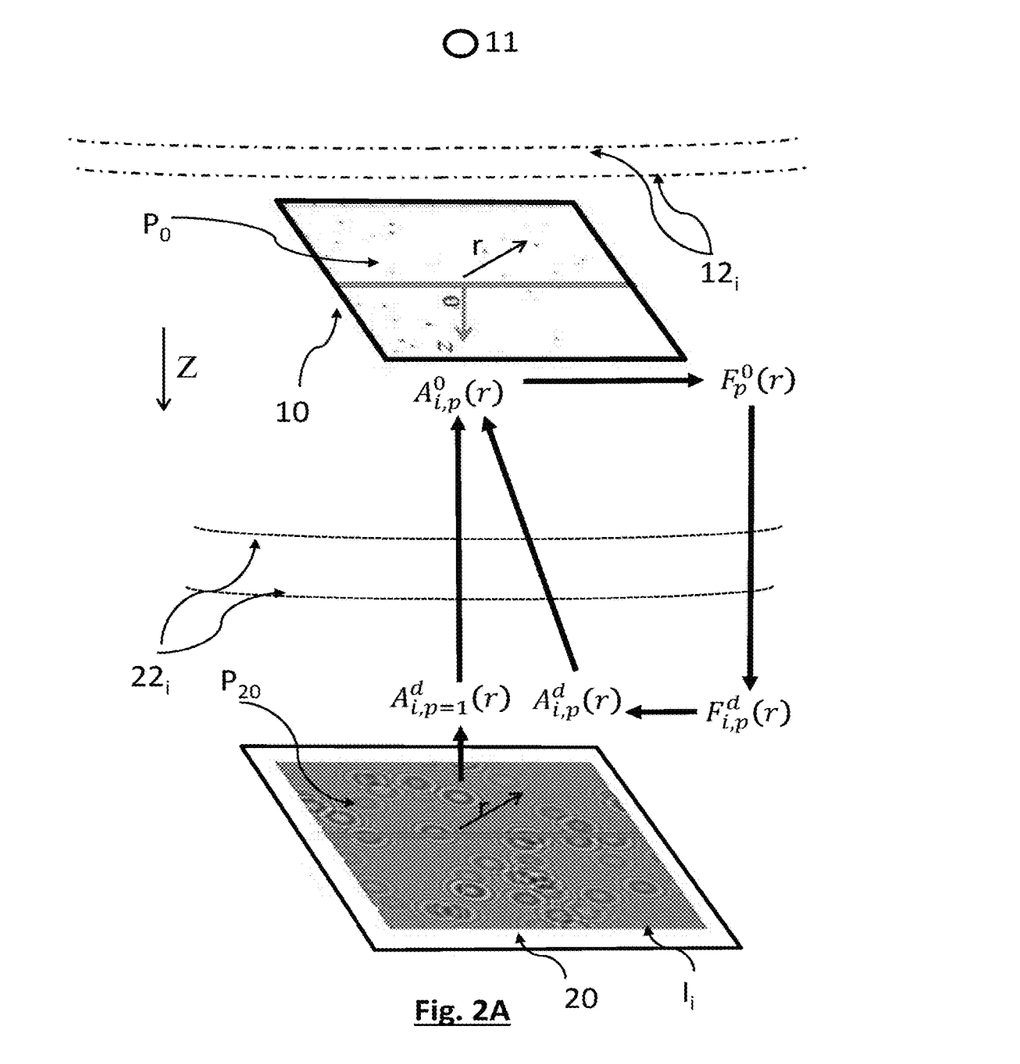
FIG. 2A shows the detection plane, on which an image is formed, and the plane in which the sample extends. This figure also illustrates the relationships between the main quantities implemented in a preferred reconstruction algorithm.
Figure 2B:
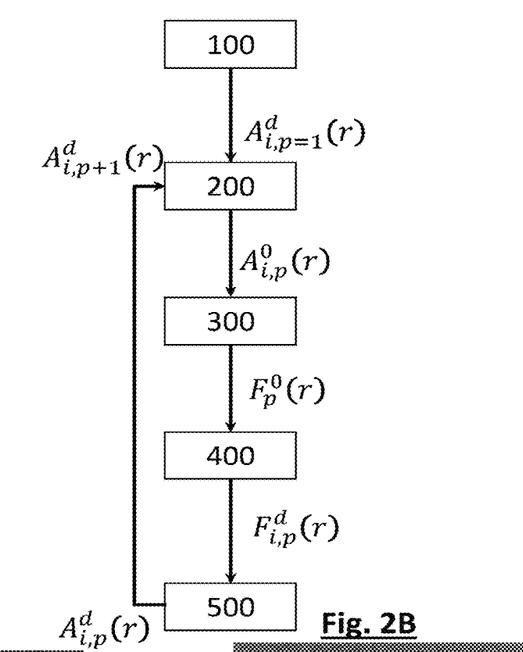
FIG. 2B shows a flowchart describing the sequence of the main steps of the reconstruction algorithm illustrated in FIG. 2A.

1st Step: Initialisation

In a first image-acquiring step 100 each elementary light source $11_i$ of the light source 11 is simultaneously activated. The image sensor acquires an image I, on the basis of which the processor forms images $I_i$ corresponding to each spectral band $λ_i$, respectively, the index i relating to the spectral band being comprised between 1 and N, N being the number of spectral bands in question. In this example, N=3. The formation of each image $I_i$ may comprise a step called a demosaicing step, including an intensity interpolation between pixels exposed to a given spectral band.

The sample is placed at an axial coordinate z=0 along the propagation axis Z. A radial coordinate, i.e. a coordinate in a plane perpendicular to the propagation axis Z, is designated by r. The plane z=d corresponds to the detection plane $P_{20}$, whereas the plane z=0 corresponds to the sample plane $P_0$.

If $I_i^{z=d}(r)=I_i^d(r)$ designates the value of the intensity collected in the spectral band $\lambda_i$ by the pixel of the image sensor of radial coordinate r in the detection plane $P_{20}$, it is possible to establish, using the image $I_i$, a complex amplitude $\alpha_i^{z=d}(r)=\alpha_i^d(r)$ of the exposing wave $22_i$ impinging said pixel of coordinate r, the modulus of which may be expressed by the expression:

$$M_i^d(r) = \sqrt{I_i^d(r)}$$

The exponent d expresses the fact that the complex amplitude is determined in the detection plane $P_{20}$, of equation z=d. As mentioned above, the complex amplitude $\alpha_i^d(r)$ has a modulus and an argument, such that:

$$\alpha_i^d(r) = M_i^d(r) e^{j\varphi_i^d(r)}$$

where:
- $M_i^d(r)$ is the modulus of the complex amplitude of the exposing light wave $22_i$ detected by the image sensor in the $i^{th}$ spectral band $\lambda_i$, at a radial coordinate r in the detection plane; and
- $\varphi_i^d(r)$ is the phase of the complex amplitude of the exposing light wave $22_i$ detected by the image sensor in the $i^{th}$ spectral band $\lambda_i$ and at said radial coordinate r in the detection plane.

However, the image sensor provides no information on the phase of the exposing light wave $22_i$. Thus, in step 100, $e^{j\varphi_i^d(r)}$ is considered to be equal to an initial arbitrary value, equal to 1 for example.

The complex amplitude $\alpha_i^d(r)$ may optionally be expressed in normalized form by the expression:

$$A_i^d(r) = \frac{\alpha_i^d(r)}{\sqrt{I_i^{mean}}}$$

where
- $I_i^{mean}$ is the mean intensity of an image formed in the $i^{th}$ spectral band $\lambda_i$; this mean intensity may be determined experimentally, by placing the image sensor 20 facing the light source 11 without the sample interposed therebetween, and by calculating the mean of the pixels of the image acquired by the image sensor 20; and
- $A_i^d(r)$ is the normalized complex amplitude of the exposing light wave $22_i$ detected by the image sensor 20 in the $i^{th}$ spectral band $\lambda_i$.

The complex amplitude may also be normalized by dividing the complex amplitude $\alpha_i^d(r)$ by $I_i^{mean}(r)$ or its square root, this term representing the light intensity, at the radial coordinate (r), measured in the absence of a sample.

The normalized complex amplitude $A_i^d(r)$ has a modulus and an argument such that:

$$A_i^d(r) = m_i^d(r) e^{j\varphi_i^d(r)}$$

where
- $m_i^d(r)$ is the modulus of the normalized complex amplitude $A_i^d(r)$ in the detection plane; and
- $\varphi_i^d(r)$ is the phase of the normalized complex amplitude, which is also the phase of the complex amplitude $\alpha_i^d(r)$, in the detection plane.

The first step 100 allows, on the basis of the image $I_i$ acquired by the image sensor 20 in the $i^{th}$ spectral band $\lambda_i$, an initial value to be attributed to each complex amplitude $\alpha_i^d(r)$ or to each normalized complex amplitude $A_i^d(r)$, this value being such that:

$$\alpha_{i,p=1}^d(r) = M_i^d(r) = \sqrt{I_i^d(r)}$$

or $$A_{i,p=1}^d(r) = m_i^d(r) = \sqrt{\frac{I_i^d(r)}{I_i^{mean}}}$$

The index p corresponds to the rank of the iteration of the iterative method described below. Since step 100 is an initialization step, the value 1 is attributed to this index.

By addressing all or some of the pixels of the image sensor 20, a complex image, or complex field, of the exposing light wave $22_i$ at the detection plane $P_{20}$ is obtained, this image representing the complex amplitudes $\alpha_i^d(r)$ or the normalized complex amplitudes $A_i^d(r)$.

In the rest of the description, only the normalized complex amplitude $A_i^d(r)$ will be considered, but the reasoning followed below is equally applicable to the complex amplitude $\alpha_i^d(r)$.

This first step is repeated for each spectral band $(\lambda_1 \ldots \lambda_N)$ detected by the image sensor 20.

$2^{nd}$ Step: Back Propagation to the Sample Plane $P_{10}$

In a second step 200, the normalized complex amplitude $A_{i,p}^0(r)$ of the exposing wave $22_i$, to which the image sensor is exposed, is estimated in the sample plane $P_0$. This estimation is performed by back propagation of the normalized complex amplitude $A_{i,p}^d(r)$ determined in the detection plane $P_{20}$, this back propagation being carried out from the detection plane $P_{20}$ to the sample plane $P_0$.

In the first iteration (p=1), the normalized complex amplitude $A_{i,p=1}^d(r) = A_1^d(r)$ obtained at the end of the first step 100 is used. In subsequent iterations (p>1), the complex amplitude resulting from the preceding iteration is used, as will be detailed below.

As described above, by calculating the product of a convolution between the complex amplitude of the exposing light wave $22_i$ associated with the spectral band $\lambda_i$, i.e. the complex amplitude determined in the detection plane z=d, and a propagation operator h, it is possible to reconstruct a complex amplitude of the same light wave at any point of spatial coordinates (r,z), and in particular in the sample plane $P_0$. In other words, the normalized complex amplitude $A_{i,p}^z(r)$ of the exposing light wave $22_i$ may be obtained, at a point of coordinates (r,z), from $A_{i,p}^{z=d}(r)$, using the operation:

$$A_{i,p}^z(r) = A_{i,p}^{z=d}(r) * h_{\lambda_i}(r, z-d),$$

where $h_{\lambda_i}$ designates the propagation operator h in the spectral band $\lambda_i$. The propagation operator may in particular be based on the Fresnel diffraction model. In this example, the propagation operator is the Fresnel-Helmholtz function such that:

$$h(r,z) = \frac{1}{j\lambda_i z} e^{j 2\pi \frac{z}{\lambda}} \exp\left(j\pi \frac{r^2}{\lambda_i z}\right)$$

where $\lambda$ designates wavelength.

Thus, $$A_{i,p}^{z=0}(r) = A_{i,p}^0(r) =$$

$$A_{i,p}^{z=d}(r) * h_{\lambda i}(r, -d) = -\frac{1}{j\lambda_i d} e^{-j2\pi \frac{d}{\lambda_i}} \int\int A_{i,p}^d(r') \exp\left(j\pi \frac{(r-r')^2}{\lambda_i d}\right) dr'$$

where:
- r' is the radial coordinates in the plane $P_{20}$ of the image sensor 20, of equation z=d;
- r is the radial coordinates in the sample plane $P_0$, which here is the reconstruction plane, of equation z=0; and
- $\lambda_i$ is the central wavelength of the spectral band.

When the reconstruction is carried out in the direction of propagation of the light, for example from the sample 10 to the image sensor 20, propagation is spoken of. When the reconstruction is carried out in the direction opposite to the direction of propagation of the light, for example from the image sensor 20 to the sample 10, back propagation is spoken of. $A_{i,p}^0(r)$ is therefore obtained by back propagating $A_{i,p}^d(r)$ over the distance d separating the detection plane $P_{20}$ from the sample plane $P_0$.

This second step is repeated for each spectral band ($\lambda_1 \ldots \lambda_N$) emitted by the light source 11 or, more generally, for each spectral band ($\lambda_1 \ldots \lambda_N$) respectively associated with each image ($I_1 \ldots I_N$) detected by the image sensor 20.

Independently of whether the complex amplitude is normalized or not, it is possible, at this stage, to establish an image of the modulus or phase of the complex amplitude $A_{i,p}^0(r)$ of each exposing light wave $22_i$, in the sample plane $P_0$, by calculating the value of $A_{i,p}^0(r)$ at various coordinates r in the sample plane $P_0$.

Each image of the modulus of the complex amplitude $A_{i,p}^0(r)$ is representative of the intensity of the exposition light wave $22_i$, within spectral band $\lambda_i$, in the sample plane $P_0$, whereas each image of the argument of the complex amplitude $A_{i,p}^0(r)$ is representative of the phase $\varphi_i^0$ of the light wave $22_i$ in the plane $P_0$ of the sample. The normalized complex amplitude $A_{i,p}^0(r)$ corresponds to a transmission function of the incident wave $12_i$ by the sample 10 at the radial coordinate r.

3rd Step: Determining the Weighting Function

In step 300, a weighting function denoted $F_p^0(r)$ that weights, in the sample plane $P_0$, the complex amplitude of the light wave transmitted by the sample in the various spectral bands $\lambda_i$, is calculated. According to this example, the weighting function $F_p^0(r)$, in the sample plane, is common to each spectral band $\lambda_i$. It is obtained by combining the normalized complex amplitudes $A_{i,p}^0(r)$ of the light wave transmitted by the sample, in the sample plane $P_0$ and in the various spectral bands $\lambda_i$. In this example, it is obtained by calculating a weighted sum of each complex amplitude determined in step 200, in the sample plane $P_0$, according to the expression:

$$F_p^0(r) = \frac{1}{\sum_i k_i} \sum_i k_i A_{i,p}^0(r)$$

where $k_i$ designates a weighting factor associated with the $i^{th}$ spectral band $\lambda_i$.

The weighting factors may be equal to one another and for example equal to ⅓.

4th Step: Propagation of the Weighting Function to the Plane of the Image Sensor Step 400 aims to propagate, from the sample plane $P_0$ to the plane $P_{20}$ of the image sensor, the weighting function $F_p^0(r)$ determined in the preceding step. Since the propagation operator h is dependent on wavelength, this propagation is carried out for each spectral band $\lambda_i$ in question.

Thus, for each spectral band $\lambda_i$, $F_{i,p}^d(r) = F_p^0(r) * h_{\lambda_i}(r, z=d)$.

When the propagation operator is a Fresnel-Helmholtz operator such as defined above, $$F_{i,p}^d(r) = \frac{1}{j\lambda_i d} e^{j2\pi \frac{d}{\lambda_i}} \int\int F_{i,p}^0(r') \exp\left(j\pi \frac{(r-r')^2}{\lambda_i d}\right) dr'.$$

As the propagation operator depends on wavelength, the same number of weighting functions is determined, in the detection plane, as there are spectral bands $\lambda_i$ in question.
- r' is the radial coordinates in the plane $P_{20}$ of the image sensor, of equation z=d;
- r is the radial coordinates in the sample plane $P_0$, which here is the reconstruction plane, of equation z=0; and
- $\lambda_i$ is the central wavelength of the spectral band in question.

5th Step: Updating the Complex Amplitude in the Plane of the Image Sensor

In step 500 the value of the weighting function $F_{i,p}^d(r)$, in the detection plane z=d, is used to update, in the same plane, the estimation of the normalized complex amplitude $A_{i,p}^d(r)$ of the exposition light wave $22_i$ to which the image sensor 20 is exposed in the spectral band $\lambda_i$.

The updating formula is:

$$A_{i,p}^d(r) = m_i^d(r) \times \frac{F_{i,p}^d(r)}{|F_{i,p}^d(r)|} = m_i^d(r) \times e^{j\varphi_{i,p}^d(r)}$$

where:
- $|F_{i,p}^d(r)|$ designates the modulus of $F_{i,p}^d(r)$;
- $m_i^d(r)$ is the modulus of the normalized initial complex amplitude $A_{i,p=1}^d$ determined from each image $I_i$ in the first step 100. This term acts as a link to the measured data;
- $\tilde{\varphi}_{i,p}^d$ is an estimation of the phase of the complex amplitude of the exposing wave $22_i$ in the $i^{th}$ spectral band $\lambda_i$; and
- $A_{i,p}^d(r)$ is the complex amplitude of the exposing light wave $22_i$ transmitted by the sample 10, within spectral band $\lambda_i$, in the plane of the image sensor 20, this complex amplitude being used in the following iteration, of rank p+1.

Following this step, a new iteration may commence, the input complex amplitude of this new iteration of rank p+1 being $A_{i,p+1}^d(r) = A_{i,p}^d(r) A_{i,p+1}^d(r) = A_{i,p}^d(r)$, this new iteration starting, for the various spectral bands in question, with the back propagation of each normalized complex amplitude $A_{i,p+1}^d(r)$ to the sample plane $P_0$, according to step 200.

Steps 200 to 500 are carried out iteratively either according to a preset number $p_{max}$ of iterations or until a convergence criterion has been reached, the latter possibly, for example, being expressed in the form of a difference between the two estimates of a given quantity obtained in two successive iterations.

At the end of the method, an estimation is obtained, in the detection plane $P_{20}$ of equation z=d and/or in the sample plane $P_0$ of equation z=0 and for each spectral band $\lambda_i$, of the complex amplitude of the exposing light wave $22_i$ transmitted by the sample 10, to 10 which light wave the image sensor 20 is exposed. Using the various reconstructed complex amplitudes $A_{i,p}^0(r)$ in the sample plane $P_0$, and in particular by forming images from the modulus or phase of said complex amplitudes, a precise representation of said plane is obtained in each of the spectral bands in question.

Although this algorithm has been described with reference to a normalized complex amplitude $A_i$ it also applies to the non-normalized complex amplitude $\alpha_i$.

From the complex amplitude obtained in the sample plane in the various spectral bands $\lambda_i$ it is possible to establish an image $I_i^0$ representing:
- either the intensity, in the sample plane $P_0$, of the exposing wave $22_i$ transmitted by the sample in a spectral band $\lambda_i$;
- or the phase $\varphi_i^0$, in the sample plane $P_0$, of the exposing wave $22_i$ transmitted by the sample in a spectral band $\lambda_i$.

It is also possible to combine the moduli or the arguments of the complex amplitude $A_{i,p}^d$, in the various spectral bands $\lambda_i$, for example in the form of a mean, so as to form an image $I^0$ representing the intensity or phase $\varphi^0$ of the exposing light wave 22 transmitted by the sample 10 and impinging the image sensor 20.

Experiments

Trials were carried out using a sample obtained from a biopsy of a human colon. Following the biopsy, the tissue was immersed in formaldehyde, which was used by way of fixative, then dehydrated by submerging it into solutions of increasing alcohol concentration. Next it was embedded into a paraffin matrix and then sectioned into thin slices of thickness comprised between 3 and 4 µm. In these trials, the impregnating liquid 25 used was an Olympus immersion oil the refractive index of which was 1.516 at 23° C. The paraffin slice, which formed the test sample $10_{test}$, was then deposited on a holding slide 15, and a drop of impregnating liquid 25 was applied to the slice. The sample 10 was then placed close to the image sensor 20 described above, such that the impregnating liquid extended between this sensor and the sample, according to the configuration illustrated in FIG. 1B.

Another tissue slice that was not wetted with the impregnating liquid was also observed, this slice forming a reference sample $10_{ref}$.

Figure 3A:
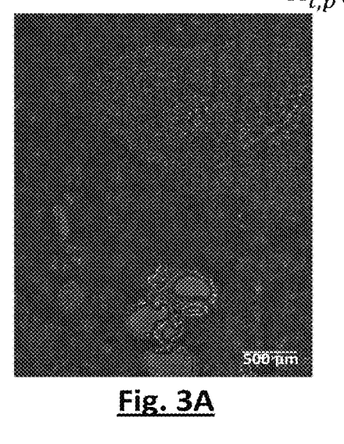
FIG. 3A shows an image of a reference sample, which image is acquired by the image sensor. The reference sample is a sample configured according to the prior art.
Figure 3B:
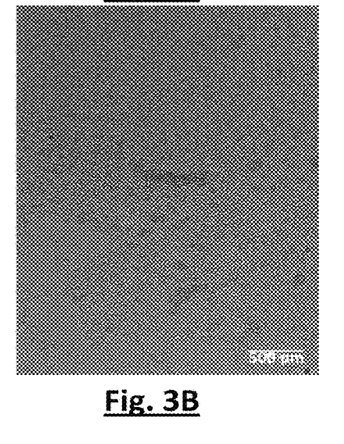
FIG. 3B shows an image of a test sample, which image is acquired by the image sensor. The reference sample and the test sample are formed from a slide of tissue sampled from an intestine. The test sample is configured according to one embodiment of the invention.

FIGS. 3A and 3B show images, which images are designated by the term hologram, acquired by the image sensor 20, these images being of the reference sample $10_{ref}$ and of the test sample $10_{test}$, respectively. The acquired images are here images in the first spectral band $\lambda_1$ (in the present case 450 nm-465 nm) represented here in grey levels. It may be observed that the image of the test sample (FIG. 3B) is clearly less contrasted than the image of the reference sample (FIG. 3A) as the test sample was made transparent by the impregnating liquid 25.

Figure 4A:
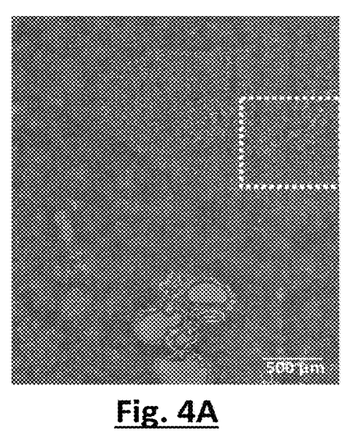
FIGS. 4A and 4B show an image of the modulus (i-e the amplitude) and what a phase image of a light wave transmitted by the reference sample, respectively.
Figure 4B:
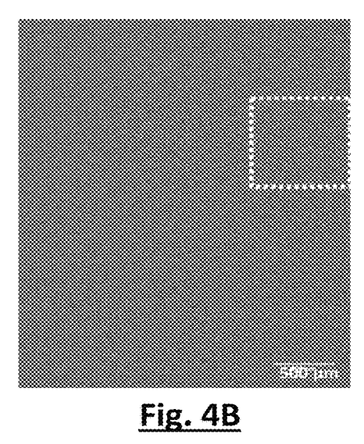

FIGS. 4A and 4B show the results of holographic reconstructions obtained from the hologram of the reference sample $10_{ref}$ illustrated in FIG. 3A, by implementing the reconstruction algorithm described with reference to FIGS. 2A and 2B. FIG. 4A shows the modulus $m_{i=1}^0(r)$ of the normalized complex amplitude $A_{i=1}^0(r)$, in the sample plane $P_0$, whereas FIG. 4B shows the phase $\varphi_{i=1}^0(r)$ of the normalized complex amplitude $A_{i=1}^0(r)$, in the sample plane $P_0$. None of these figures is truly exploitable.

Figure 4C:
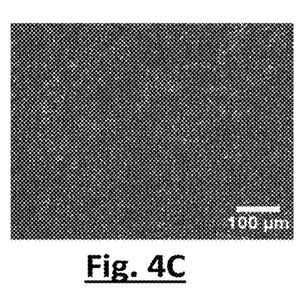
FIGS. 4C and 4D show a detail of FIGS. 4A and 4B, respectively.
Figure 4D:
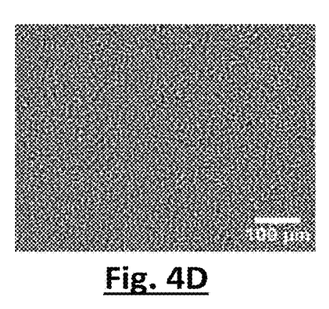

FIGS. 4C and 4D respectively correspond to details of the images 4A and 4B in the regions of interest bounded by the dotted frames.

Figure 5A:
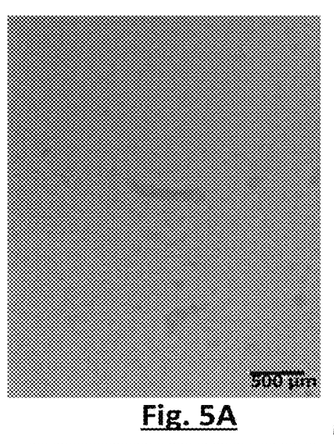
FIGS. 5A and 5B show an image of the modulus and a phase image of a light wave transmitted by the test sample, respectively.
Figure 5B:
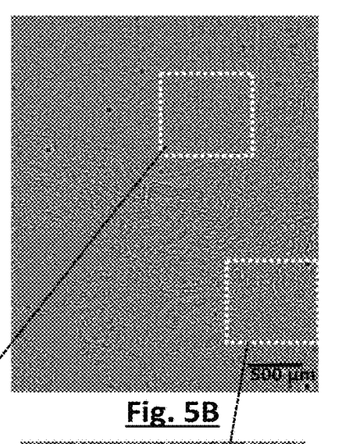
Figure 5C:
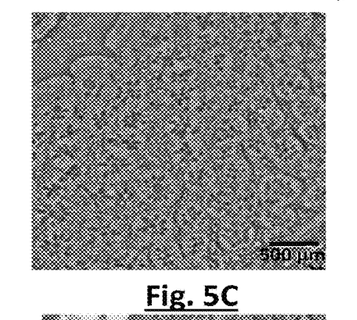
FIGS. 5C and 5D show a detail of FIGS. 5A and 5B, respectively.
Figure 5D:
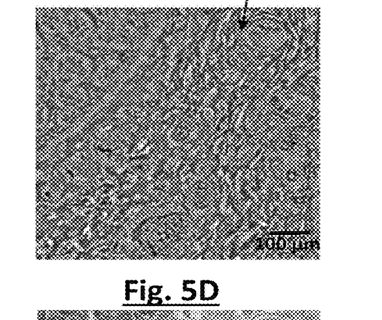

FIGS. 5A and 5B show the results of holographic reconstructions obtained from the hologram of the test sample $10_{test}$ illustrated in FIG. 3B. FIG. 5A shows the modulus $m_{i=1}^0(r)$ of the normalized complex amplitude $A_{i=1}^0(r)$, in the sample plane $P_0$, whereas FIG. 5B shows the phase $\varphi_{i=1}^0(r)$ of the normalized complex amplitude $A_{i=1}^0(r)$ in the sample plane $P_0$. FIG. 5A contains no exploitable information, this being expected given that the test sample $10_{test}$ was made transparent by the impregnating liquid 25. In contrast, FIG. 5B is particularly rich in information and is an exploitable representation of the observed sample. FIGS. 5C and 5D correspond to details of the image 5B, in the regions of interest bounded, in FIG. 5B, by the dotted frames. The implemented reconstruction method is rapid: the duration of the acquisition is only 0.5 seconds whereas the duration of the reconstruction is of the order of one second, i.e. 1.5 seconds to obtain an exploitable image, the field of observation being 9.7 mm².

Figure 5E:
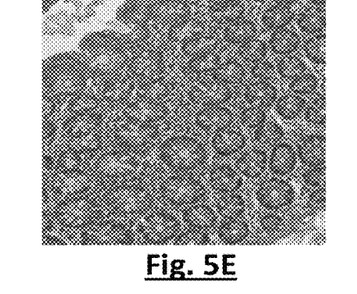
FIGS. 5E and 5F are views of the test sample, which views are obtained according to a conventional microscopy modality, the field of observation corresponding to the details illustrated in FIGS. 5A and 5B, respectively.
Figure 5F:
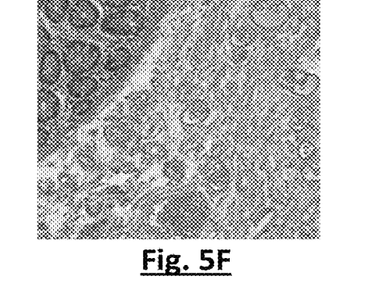

The test sample $10_{test}$ was observed by microscopy after haematoxylin-eosin-saffron (HES) staining, this type of staining being common in the field of histology. FIGS. 5E and 5F show images corresponding substantially to the regions of interest shown in FIGS. 5C and 5D, respectively. The consistency between the reconstructed phase image and the image obtained by microscope is obvious, this attesting to the reliability and advantageousness of the invention.

Figure 6A:
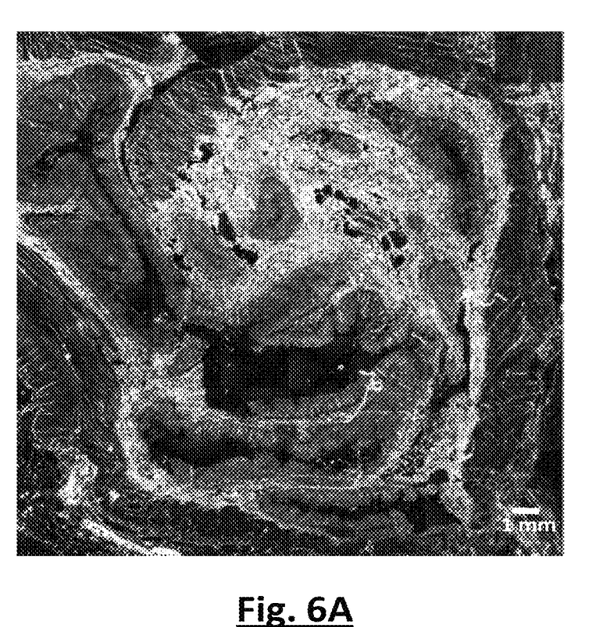
FIG. 6A shows what a phase image of the test sample.
Figure 6B:
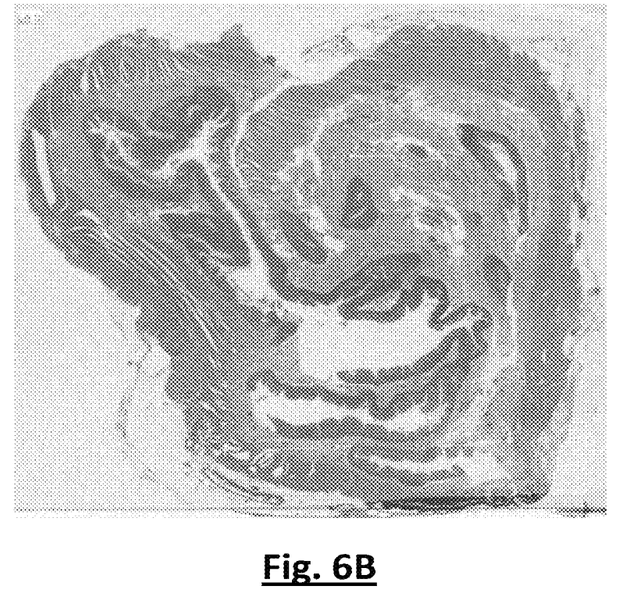
FIG. 6B is an image obtained from the same sample according to a conventional microscopy modality.

The relative position of the test sample $10_{test}$ and of the image sensor 20 was modified, by virtue of the translation stage 40. A representation of all of the test sample was obtained by scanning. FIG. 6A shows an image of the phase $\varphi_{i=1}^0(r)$ of the normalized complex amplitude $A_{i=1}^0(r)$ in the first spectral band $\lambda_1$, said image having been reconstructed in the sample plane $P_0$ after application of a high-pass variance filter. Such a filter allows the value of the variance in the vicinity of each pixel to be calculated, the value of the pixel being replaced by the value of the variance thus calculated. The vicinity of each pixel may for example be a zone of 5 by 5 pixels. Other high-pass filters, for example of the type used in edge detection, could be used. FIG. 6B shows an observation of the test sample by conventional microscope i.e. by a reference method. The degree of consistency between these two images is high.

Generally, an image of the phase of the wave transmitted by the sample, i.e. the wave to which the image sensor is exposed, represents a spatial distribution of the refractive index of the sample, in so far as the thickness of the sample may be considered to be constant, which is the case when slices of biological tissues are being observed.

The method described above allows a representation of a sample to be obtained that is exploitable in histology and diagnosis-assistance, and has the following advantages:
- with respect to a microscope, the field of observation is larger, thereby allowing a sample of large area to be observed much more rapidly:
- the method does not require the sample to be stained; and
- with respect to other holographic methods, the impregnation of a sample with an impregnating liquid allows holograms to be obtained the quality of which is high enough to obtain reconstructed images allowing correct and rapid characterization of the sample.

The invention will possibly be used to observe a tissue sample in histology but also, outside of the field of biology, any porous sample the transparency of which is increased under the effect of impregnation by an impregnating liquid.

The targeted applications may be in the field of food processing, the analysis of industrial samples (filters for example) or in the field of environmental inspection.

The invention claimed is:

1. A method for observing a porous sample, the method comprising:
   illuminating said sample with a light source that emits an incident light wave propagating towards the sample;
   applying an impregnating fluid to the sample such that the sample is impregnated with the impregnating liquid, the impregnating liquid having a refractive index that is greater than 1, and the sample is made transparent or translucent after the impregnating liquid has been applied;
   acquiring, using an image sensor extending in a detection plane, an image of the sample, the sample being placed between the light source and the image sensor, the image being representative of an exposing light wave to which the image sensor is exposed;
   applying a propagation operator to the image to form a reconstructed image representative of the exposing light wave, in a plane passing through said sample, wherein
   the impregnating liquid extends from the sample to the image sensor, and
   the reconstructed image is established from a phase, in the plane passing through the sample, of the exposing light wave.

2. The method according to claim 1, wherein the sample is a slice of biological tissue.

3. The method according to claim 1, wherein the impregnating liquid has a refractive index between 1.2 and 1.8.

4. The method according to claim 1, wherein the image sensor comprising a plurality of pixels.

5. The method according to claim 1, wherein the impregnating liquid is applied to the sample or to the image sensor and then a distance between the sample and the image sensor is decreased until the impregnating liquid extends from the sample to the image sensor.

6. The method according to claim 1, further comprising:
   acquiring a plurality of images, each image being acquired in a different spectral band, wherein
   the propagation operator is applied to the image according to the following substeps:
      a) determining, from each image acquired in a spectral band, an initial complex amplitude of the exposing light wave in said spectral band, in the detection plane;
      b) based on each complex amplitude established in said detection plane, in each spectral band, determining a complex amplitude of the exposing light wave in each spectral band, in the plane in which the sample extends;
      c) combining a plurality of complex amplitudes, in various spectral bands, to calculate a weighting function in the sample plane;
      d) projecting said weighting function into the detection plane so as to obtain, for each spectral band, a final weighting function in said detection plane; and
      e) updating each complex amplitude of the exposing light wave in each spectral band, in the detection plane, using said final weighting function.

7. The method according to claim 6, wherein the propagation operator is applied according to
   f) forming the reconstructed image representative of an argument, in the plane of the sample, of the complex amplitude of the exposing light wave transmitted by the sample in at least one spectral band.

8. A method for observing a porous sample, the method comprising:
   illuminating said sample with a light source that emits an incident light wave propagating towards the sample;
   applying an impregnating fluid to the sample such that the samplers impregnated with the impregnating liquid, the impregnating liquid having a refractive index that is greater than 1, and the sample is made transparent or translucent after the impregnating liquid has been applied;
   acquiring, using an image sensor extending in a detection plane, an image of the sample, the sample being placed between the light source and the image sensor, the image being representative of an exposing light wave to which the image sensor is exposed;
   applying a propagation operator to the image to form a reconstructed image representative of the exposing light wave, in a plane passing through said sample, wherein
   wherein a transparent slide is placed between the sample and the image sensor, the impregnating liquid extending between the sample and said transparent slide, and
   the reconstructed image is established from a phase in the plane passing through the sample, of the exposing light wave.

9. The method according to claim 8, wherein the sample is a slice of biological tissue.

10. The method according to claim 8, wherein the impregnating liquid has a refractive index between 1.2 and 1.8.

11. The method according to claim 8, further comprising:
    acquiring a plurality of images, each image being acquired in a different spectral band, wherein
    the propagation operator is applied to the image according to the following substeps:
       a) determining, from each image acquired in a spectral band, an initial complex amplitude of the exposing light wave in said spectral band, in the detection plane;
       b) based on each complex amplitude established in said detection plane, in each spectral band, determining a complex amplitude of the exposing light wave in each spectral band, in the plane in which the sample extends;
       c) combining a plurality of complex amplitudes, in various spectral bands, to calculate a weighting function in the sample plane;
       d) projecting said weighting function into the detection plane so as to obtain, for each spectral band, a final weighting function in said detection plane; and
       e) updating each complex amplitude of the exposing light wave in each spectral band, in the detection plane, using said final weighting function.

12. The method according to claim 11, wherein the propagation operator is applied according to
    f) forming the modified image representative of an argument, in the plane of the sample, of the complex amplitude of the exposing light wave transmitted by the sample in at least one spectral band.

* * * * *